US009132536B2

(12) United States Patent
Nino et al.

(10) Patent No.: US 9,132,536 B2
(45) Date of Patent: Sep. 15, 2015

(54) CANNULATED ULTRA HIGH TORQUE DEVICE

(75) Inventors: John Nino, Simi Valley, CA (US); David Ivinson, Camarillo, CA (US)

(73) Assignee: ECA Medical Instruments, Newbury Park, CA (US)

( * ) Notice: Subject to any disclaimer, the term of this patent is extended or adjusted under 35 U.S.C. 154(b) by 354 days.

(21) Appl. No.: 13/695,818

(22) PCT Filed: Apr. 29, 2011

(86) PCT No.: PCT/US2011/034618
§ 371 (c)(1),
(2), (4) Date: Nov. 26, 2012

(87) PCT Pub. No.: WO2011/139905
PCT Pub. Date: Nov. 10, 2011

(65) Prior Publication Data
US 2013/0205569 A1   Aug. 15, 2013

Related U.S. Application Data

(60) Provisional application No. 61/332,171, filed on May 6, 2010.

(51) Int. Cl.
*B23P 17/00* (2006.01)
*B25B 23/142* (2006.01)
(Continued)

(52) U.S. Cl.
CPC .......... *B25B 23/142* (2013.01); *A61B 17/8883* (2013.01); *B25B 15/00* (2013.01);
(Continued)

(58) Field of Classification Search
CPC ...... B25B 13/463; B25B 15/02; B25B 15/04; B25B 23/14; B25B 23/141; B25B 23/142; B25B 23/1427
USPC .......................... 29/460, 525.11; 81/473, 475
See application file for complete search history.

(56) References Cited

U.S. PATENT DOCUMENTS 5,576,501 A * 11/1996 Huang ........................ 73/862.23
6,439,086 B1 * 8/2002 Bahr ............................... 81/467
(Continued)

FOREIGN PATENT DOCUMENTS

CN       2238511      10/1996
CN       1505555       6/2004

OTHER PUBLICATIONS

NASA, "Human Performance Capabilities," 25 Pages.*
(Continued)

*Primary Examiner* — Jacob Cigna
(74) *Attorney, Agent, or Firm* — Baker Hostetler LLP; Mark H. Krietzman

(57) ABSTRACT

A torque-limiting device may include a shaft extending axially through upper and lower shanks and a spring to connect to a nut. The upper and lower shanks may be under a force from the spring and further configured to selectively engage within a predetermined torque limit and disengage at above the predetermined torque limit. Accordingly, the shaft may receive torque up to the predetermined limit as provided by a user operating a handle of the torque-limiting device. The torque-limiting device may be disposable, reusable, economical, and have high torque capabilities. The shaft may include a lumen extending there through, and through which a variety of devices and materials may be delivered to a workpiece.

23 Claims, 8 Drawing Sheets

(51) Int. Cl.
    *A61B 17/88*    (2006.01)
    *B25B 15/00*    (2006.01)
    *A61B 19/00*    (2006.01)
(52) U.S. Cl.
    CPC ....... *B25B23/1427* (2013.01); *A61B 2019/301* (2013.01); *Y10T 29/49888* (2015.01); *Y10T 29/49963* (2015.01)

(56) References Cited

U.S. PATENT DOCUMENTS

| | | | |
|---|---|---|---|
| 7,181,997 B1 * | 2/2007 | Rinner et al. | 81/58.4 |
| 7,334,509 B1 * | 2/2008 | Gao | 81/475 |
| 7,475,619 B2 | 1/2009 | Chiu et al. | |
| 7,938,046 B2 * | 5/2011 | Nino et al. | 81/475 |
| 2006/0016300 A1 | 1/2006 | Bubel | |
| 2006/0248988 A1 * | 11/2006 | Bennett | 81/62 |
| 2006/0278051 A1 | 12/2006 | Gauthier et al. | |
| 2007/0289391 A1 * | 12/2007 | Gao | 73/862.21 |
| 2009/0293687 A1 | 12/2009 | Nino et al. | |

OTHER PUBLICATIONS

Chinese Office Action dated Sep. 4, 2014, issued in Chinese patent application 20118033625.2.

* cited by examiner

CANNULATED ULTRA HIGH TORQUE DEVICE

RELATED APPLICATION

This application claims the full Paris Convention benefit of and priority to U.S. Provisional Patent Application Ser. No. 61/332,171 filed May 6, 2010, the contents of which are incorporated by reference herein in its entirety, as if fully set forth herein. This application also incorporates by reference U.S. patent application Ser. No. 12/131,731, filed Jun. 2, 2008, as if fully set forth herein in its entirety.

BACKGROUND

1. Field

This disclosure relates to a driver tool and, in particular, to a medical use torque-limiting driver that disengages at a predetermined torque limit.

2. General Background

Torque is a measure of force acting on an object that causes that object to rotate. In the case of a driver and a fastener, this measurement can be calculated mathematically in terms of the cross product of specific vectors:

$$\tau = r \times F$$

Where r is the vector representing the distance and direction from an axis of a fastener to a point where the force is applied and F is the force vector acting on the driver.

Torque has dimensions of force times distance and the SI unit of torque is the Newton meter (N-m). The joule, which is the SI unit for energy or work, is also defined as an N-m, but this unit is not used for torque. Since energy can be thought of as the result of force times distance, energy is always a scalar whereas torque is force cross-distance and so is a vector-valued quantity. Other non-SI units of torque include pound-force-feet, foot-pounds-force, ounce-force-inches, meter-kilograms-force, inch-ounces or inch-pounds.

Torque-limiting drivers are widely used throughout the medical industry. These torque-limiting drivers have a factory pre-set torque to ensure the accuracy and toughness required to meet a demanding surgical environment.

The medical industry has made use of both reusable and disposable torque-limiting drivers. In a surgical context, there is little room for error and these drivers must impart a precise amount of torque.

Reusable drivers require constant recalibration to ensure that the driver is imparting the precise amount of torque. Recalibration is a cumbersome task but must be done routinely. Such reusable devices also require sterilization.

Disposable drivers are an alternative to the reusable drivers. Once the driver has been used, it is discarded.

Disposable drivers are traditionally used for low torque applications. The standard torque values in these applications typically range from about 4 to about 20 inch-ounces. It has, however, been a challenge to develop a reliable disposable driver capable of imparting higher torques for larger applications.

Piecemeal drivetrain systems have been developed to gear-up or otherwise impart greater torque with disposable devices. Such piecemeal systems provide interchangeability of parts to a device, within which torque is transferred from part-to-part of a piecemeal system.

SUMMARY

Briefly stated, torque devices according to implementations of the present disclosure obviate the shortfalls of piecemeal systems by reducing the number of part-to-part transitions of torque.

According to aspects of one or more exemplary implementations, disclosed is a torque-limiting driver comprising: a body having a handle; an upper cylindrical shank; a lower cylindrical shank having a drive socket; a nut; a spring between the upper cylindrical shank and the nut, wherein the spring is configured to apply a force across the upper cylindrical shank and the lower cylindrical shank; a shaft having a workpiece-engaging tip and a drive connection engaged within the drive socket of the lower cylindrical shank, the shaft extending axially through the lower cylindrical shank, the upper cylindrical shank, and the spring and connected to the nut, and the shaft having a lumen extending across an axial length of the shaft; wherein the upper cylindrical shank and the lower cylindrical shank engage for relative rotation, and wherein the upper cylindrical shank and the lower cylindrical shank disengage when a predetermined torque limit is exceeded.

The lumen may form a tube, and/or enclose a tube advanceable within said lumen. The lumen and/or tube may be configured to deliver a biologic material. The biologic material may be an adhesive. The biologic material may be a growth stimulant. The lumen is an enclosure through which a guidewire is advanceable. The drive socket may be a square drive socket and the drive connection may be a square drive connection. The shaft may include a threading that is threaded onto the nut. A force provided by the spring may securely maintain the drive connection of the shaft engaged within the drive socket of the lower cylindrical shank. The nut may include a lower portion having an outer diameter substantially equal to an inner diameter of the spring and extending axially through at least a portion of the spring.

The torque-limiting driver may further comprise at least two washers between the spring and the upper cylindrical shank. The torque-limiting driver may further comprise a washer between the lower cylindrical shank and the body. The torque-limiting driver may further comprise a washer between the spring and the nut.

The upper cylindrical shank and the lower cylindrical shank may each have a plurality of teeth and an axial bore, the teeth having a vertical face, an inclined face and a substantially flat peak, wherein the inclined face is defined by a first radius of curvature that transitions to the substantially flat peak and wherein the teeth spiral around the axial bore. The vertical face may terminate in a second radius of curvature that transitions to the substantially flat peak and wherein the second radius of curvature is smaller than the first radius of curvature. The substantially flat surface may be wider at the outer radius than at the inner radius and wherein the substantially flat surface is perpendicular to the axis of the upper and lower shank. The transition from the first radius of curvature and second radius of curvature to the substantially flat peak may be smooth.

The predetermined torque limit may be at least 1 inch-pound. The predetermined torque limit may be between about 70 inch-pounds and about 150 inch-pounds.

According to aspects of one or more exemplary implementations, disclosed is a method, comprising: providing to a workpiece a torque-limiting driver comprising: a body having a handle; an upper cylindrical shank; a lower cylindrical shank having a drive socket; a nut; a spring between the upper cylindrical shank and the nut, wherein the spring is configured to apply a force across the upper cylindrical shank and the lower cylindrical shank; a shaft having a workpiece-engaging tip and a drive connection engaged within the drive socket of the lower cylindrical shank, the shaft extending axially through the lower cylindrical shank, the upper cylindrical shank, and the spring and connected to the nut, and the shaft having a lumen extending across an axial length of the shaft; applying an applied torque to the torque-limiting driver, whereby the upper cylindrical shank and the lower cylindrical shank engage for relative rotation if the applied torque does not exceed the predetermined torque limit, and whereby the upper cylindrical shank and the lower cylindrical shank disengage if the applied torque exceeds the predetermined torque limit; and delivering a biologic material to the workpiece through the lumen.

The biologic material may be an adhesive. The biologic material may be a growth stimulant.

According to aspects of one or more exemplary implementations, disclosed is a method, comprising: providing to a workpiece a torque-limiting driver comprising: a body having a handle; an upper cylindrical shank; a lower cylindrical shank having a drive socket; a nut; a spring between the upper cylindrical shank and the nut, wherein the spring is configured to apply a force across the upper cylindrical shank and the lower cylindrical shank; a shaft having a workpiece-engaging tip and a drive connection engaged within the drive socket of the lower cylindrical shank, the shaft extending axially through the lower cylindrical shank, the upper cylindrical shank, and the spring and connected to the nut, and the shaft having a lumen extending across an axial length of the shaft; wherein the upper cylindrical shank and the lower cylindrical shank engage for relative rotation, and wherein the upper cylindrical shank and the lower cylindrical shank disengage when a predetermined value of torque is exceeded; aligning the torque-limiting driver relative to the workpiece by use of a guidewire delivered through the lumen of the shaft; and applying an applied torque to the torque-limiting driver, whereby the upper cylindrical shank and the lower cylindrical shank engage for relative rotation if the applied torque does not exceed the predetermined torque limit, and whereby the upper cylindrical shank and the lower cylindrical shank disengage if the applied torque exceeds the predetermined torque limit.

DRAWINGS

The above-mentioned features of the present disclosure will become more apparent with reference to the following description taken in conjunction with the accompanying drawings wherein like reference numerals denote like elements and in which.

Figure 1:
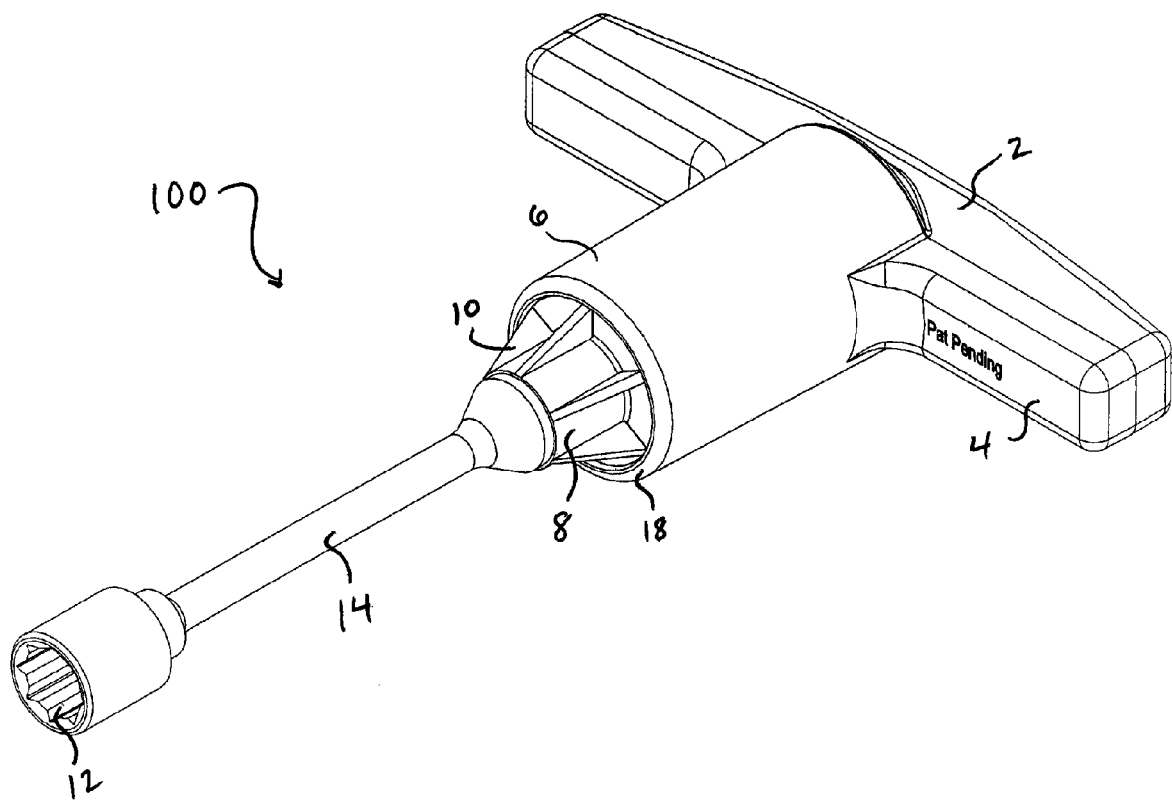
FIG. 1 shows a perspective view of some aspects of a driver.

As shall be appreciated by those having ordinary skill in the art, the figures are not to scale, and modifications to scale within a figure or across the figures are considered within the present disclosure.

FURTHER DESCRIPTION

According to one or more exemplary implementations, as shown in FIGS. 1-8, torque-limiting driver 100 may be provided. Torque-limiting driver 100 may have a generally T-shaped handle or other structure to facilitate use by a user. For example, the handle may by "T-shaped". The handle may include arms 4 at one end of an axially extending generally hollow cylindrical body 6. Cap 2 covers the same end of the handle. Cylindrical end 18 terminates cylindrical body 6 toward tip 12 of shaft 14. Cap 2 may be snap-fitted to cylindrical body 6, or may be welded, adhered, or attached by any equivalent thereof.

An exemplary implementation shows, at least in part, at cylindrical end 18, lower shank 700 provided, having an annularly tapering body and nose cone 8 along its length. Lower shank 700 may have a plurality of support flanges 10 that add strength while saving material. At one end, lower shank 700 tapers to drive socket 9 at the end of the nose cone 8 molded to engage drive connection 16 of shaft 14. An exemplary implementation shows, at least in part, shaft 14 provided, at one end, with workpiece-engaging tip 12, adapted for engagement with an associated workpiece, such as a fastener or the like. Workpiece-engaging tip 12 is shown to be a socket wrench, but could be a screwdriver, wrench, or any other tool arrangement. At an opposite end, lower shank 700 has a plurality of teeth 82 arranged in a crown gear formation, with circumferential rim 31 extending radially outward and an internal axial bore to accommodate at least a portion of shaft 14 extending there through.

Figure 5:
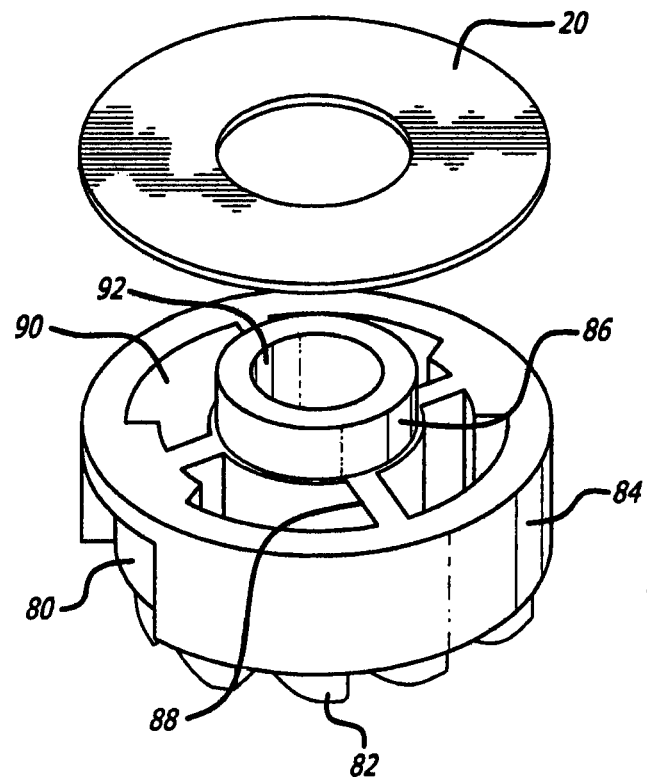
FIG. 5 shows a perspective view of some aspects of an upper shank.

According to aspects of one or more exemplary implementations, inside cylindrical body 6 a clutch assembly is disposed. The clutch assembly includes upper shank 800 for forcibly engaging lower shank 700. Upper shank 800 has a bottom face that has a plurality of teeth 82 arranged in a crown gear formation and circumferential rim 83 extending radially outward. As shown in FIG. 5, upper shank 800 includes outer cylindrical shank 84 and axial bore 92 through inner shank 86. Inner shank 86 and outer shank 84 are connected via inner supports 88, leaving upper shank 800 substantially hollow with internal spaces 90 on a top face. Alternatively, upper shank 800 may be of a single contiguous piece.

Figure 2A:
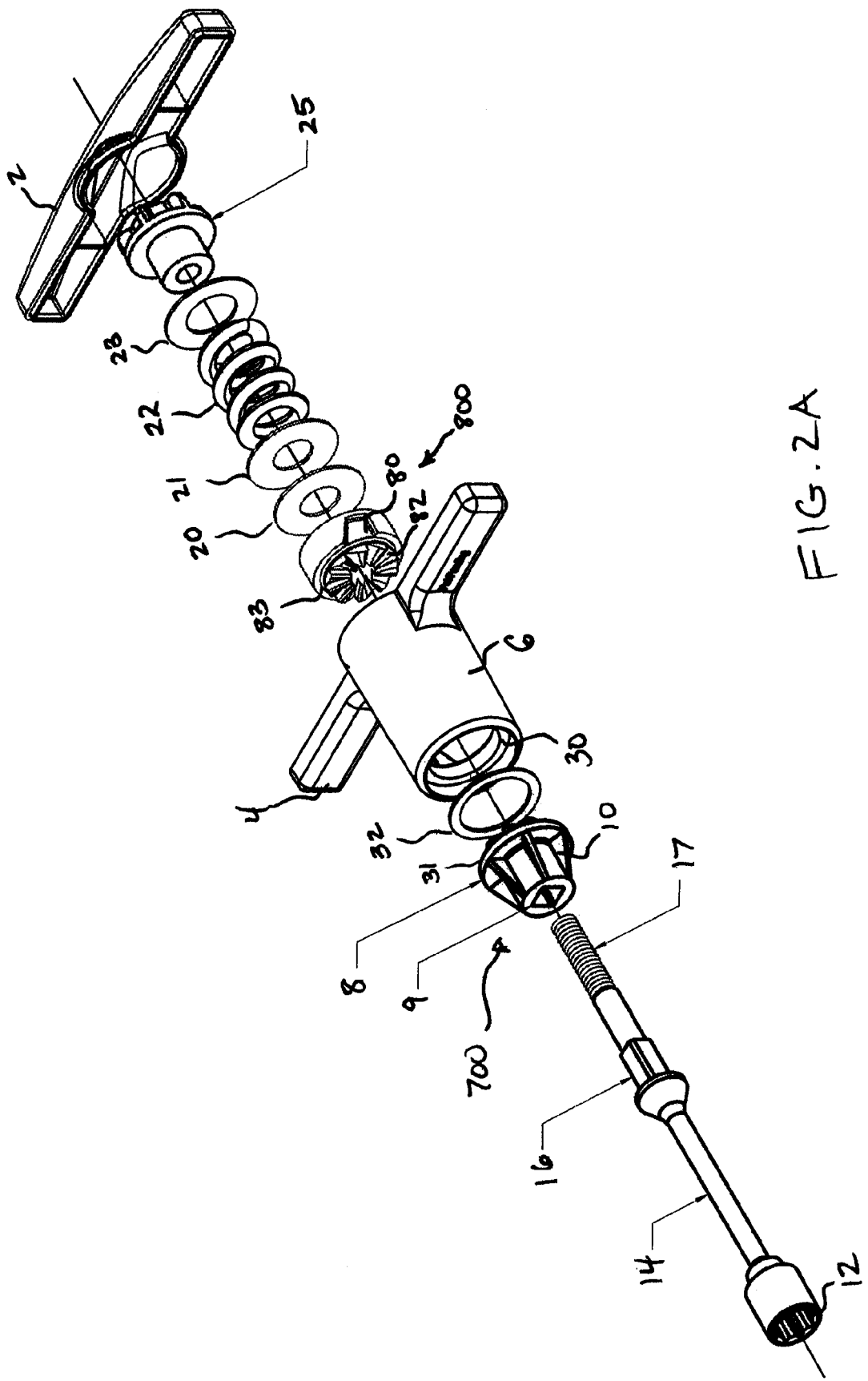
FIG. 2A shows an exploded view of some aspects of a driver.
Figure 2B:
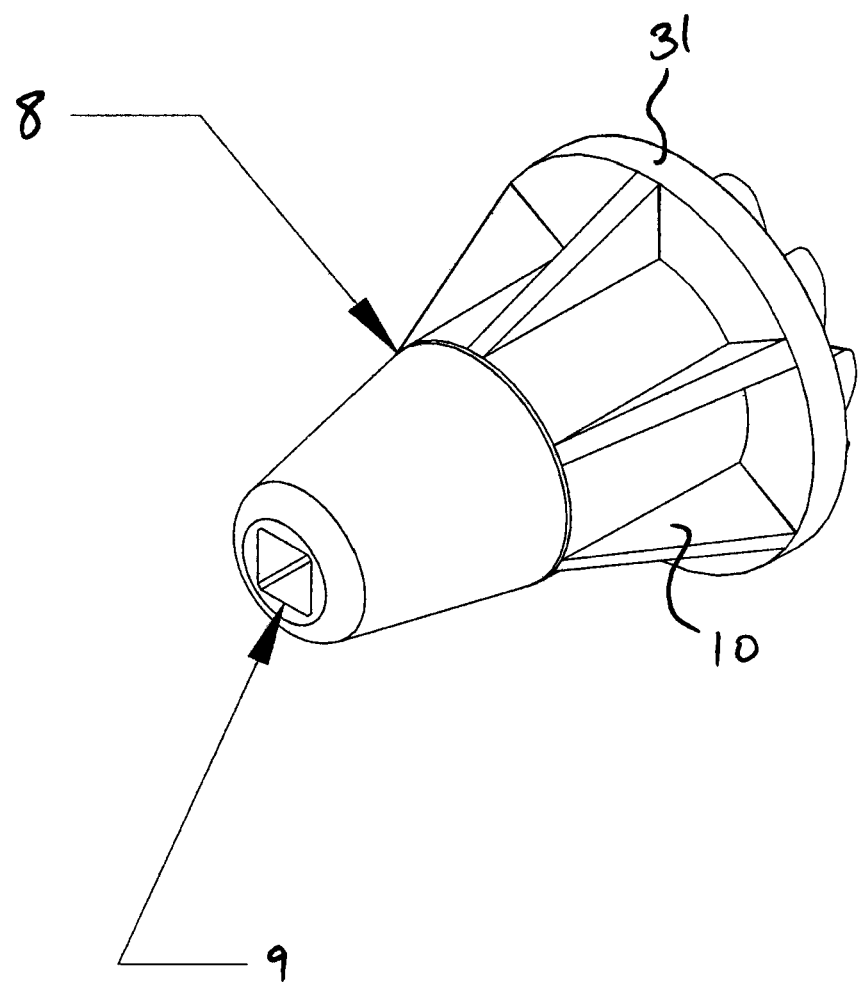
FIG. 2B shows a perspective view of some aspects of a nose cone.

According to one or more exemplary implementations, upper shank 800 includes at least one recess 80 on a side of outer shank 84. Recess 80 is provided as a cylindrical cut, relief or recess into the side of the outer shank and may be provided as a square or rectangular cut or the cut may have a slanted side or sides relative to the axis of upper shank 800, as shown in FIG. 2.

In assembly, drive connection 16 of shaft 14 is received into drive socket 9 of lower shank 700. Washer 32 may be provided between circumferential rim 31 of lower shank 700 and circumferential flange 30 extending radially inward within the hollow of cylindrical body 6. Washer 32 may be of a polymer or other material having low coefficient of friction. Alternatively, circumferential rim 31 of lower shank 700 may be provided flush against circumferential flange 30 of cylindrical body 6. The opposite side of circumferential flange 30 receives circumferential rim 83 of upper shank 800, allowing teeth 82 of lower shank 700 to engage teeth 82 of upper shank 800 when a torque is applied.

Figure 3:
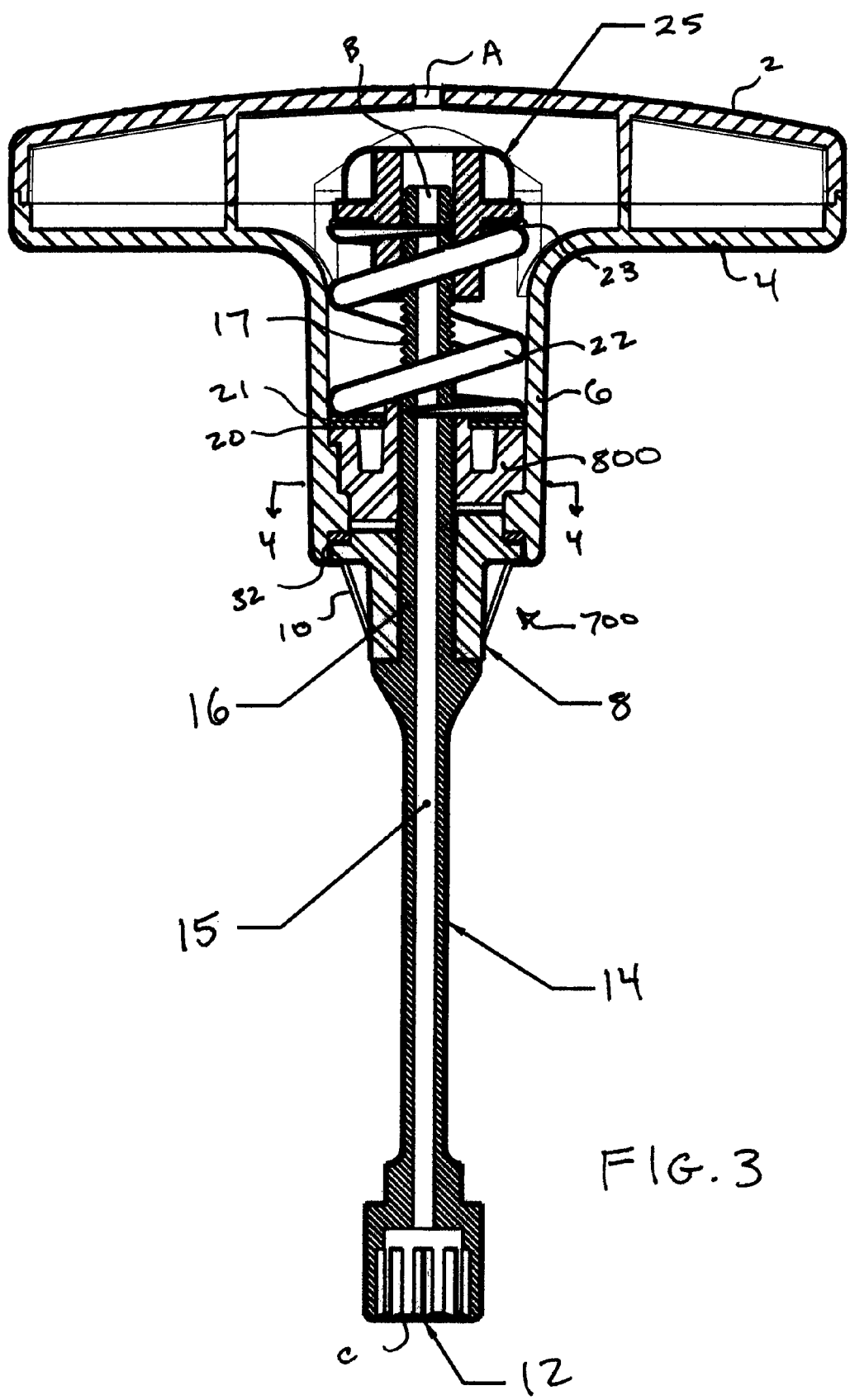
FIG. 3 shows a cross sectional view of some aspects of a driver.
Figure 4:
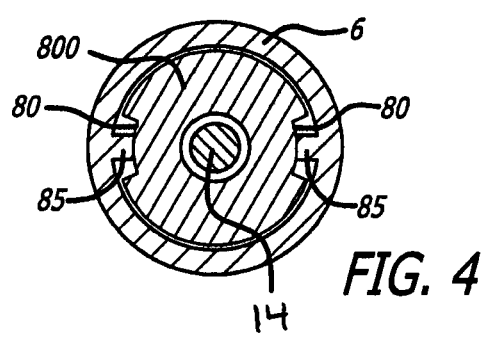
FIG. 4 shows a cross sectional view of some aspects of a driver.

According to aspects of one or more exemplary implementations, integrally formed within cylindrical body 6, protrusion 85 mates with recess 80 of upper shank 800. FIG. 3 and FIG. 4 illustrate protrusion 85 in relation with recess 80. Protrusion 85 extends inward in a radial fashion and has a length along the axis of cylindrical body 6 for relative moveable engagement within recess 80. This engagement provides a locking mechanism of shaft 14 relative to the handle via upper shank 800 when pressure is applied across lower shank 700 and upper shank 800. Recess 80 is provided circumferentially wider than protrusion 85 for allowing cylindrical body 6 and the handle to rotate in reverse a predetermined distance from a locked position without subsequent reverse rotation of workpiece-engaging tip 12. Thus, at least one recess 80 and at least one protrusion 85 lock the handle in one direction providing the necessary torque to drive a fastener and allow for a predetermined amount of reverse rotation before unscrewing the fastener.

According to aspects of one or more exemplary implementations, force is applied across lower shank 700 and upper shank 800 via spring 22 within cylindrical body 6. Inside cylindrical body 6, shown in FIG. 2 and FIG. 5, washer 20 and washer 21 are provided between upper shank 800 and spring 22. Washer 20 and washer 21 transfer pressure from spring 22 over the top face of upper shank 800. At an end of spring 22 opposite upper shank 800, washer 23 and nut 25 hold spring 22 in a relatively compressed state. Washer 23 may be provided between nut 25 and spring 22 to facilitate relative rotation of nut 25 and spring 22.

According to one or more exemplary implementations, shaft 14 having threading 17 at an end opposite workpiece-engaging tip 12 engages a complementary threading within nut 25, thereby imparting pressure between the respective teeth 82 of lower shank 700 and upper shank 800. Spring 22 and nut 25 provide the proper tensioning and biasing for the clutch assembly and, generally, the nut 25 is adjustable relative to shaft 14 to provide proper tension and calibration.

According to aspects of one or more exemplary implementations, various materials may be used for the components of driver 100. According to some exemplary implementations, at least one of body 6, nut 25, lower shank 700, and upper shank 800 is of a plastic material or a composite including plastic. Plastic and other economical equivalents improve cost efficiency of production while providing high tensile strength, resistance to deformation, etc. Effective materials include plastics, resins, polymers, imides, fluoropolymers, thermoplastic polymers, thermosetting plastics, and the like as well as blends or mixtures thereof. According to aspects of one or more exemplary implementations, at least one of lower shank 700 and upper shank 800 is of or includes at least one material that lubricous or otherwise reduces friction. The presence of a friction-reducing material allows geometric aspects of the engagement between lower shank 700 and upper shank 800 to govern whether teeth engage or disengage, thereby improving precision of the device.

According to aspects of one or more exemplary implementations, materials and components of drive 100 are resistant to sterilization, cleaning, and preparation operations. For example, drive 100 and parts thereof are configured to withstand sterilization by methods including radiation (e.g., gamma rays, electron beam processing), steam (e.g., autoclave), detergents, chemical (e.g., Ethylene Oxide), heat, pressure, inter alia. For example, materials for drive 100 may be selected according to resistance to one or more selected sterilization techniques.

According to aspects of one or more exemplary implementations, shaft 14 is of a rigid material. For example, shaft 14 may be of a metal, such as stainless steel. According to some exemplary implementations, high torque capabilities of drive 100 are, at least in part, provided by features that maintain an effective engagement between drive connection 16 of shaft 14 and drive socket 9 of lower shank 800. For example, some exemplary implementations are provided to improve the ability of drive 100 to maintain its grip on shaft 14 up to a greater range of torque.

According to aspects of one or more exemplary implementations, a single integrated shaft 14 spans the distance between workpiece-engaging tip 12 and an engagement point with nut 25. This configuration enables greater torque capabilities than a piecemeal or fragmented set of interconnected components. This reduces the number of interconnections between a source of a torque and a location to which the torque is transferred.

According to one or more exemplary implementations, shaft 14 having drive connection 16 between opposing extensions stabilizes drive connection 16 within drive socket 9. Placement of drive connection 16 at a medial segment of shaft 14—rather than at an end thereof—facilitates a more stable engagement between drive connection 16 and drive socket 9, thereby increasing the ability of engagement to transfer high amounts of torque.

According to one or more exemplary implementations, an engagement of drive connection 16 within drive socket 9 is maintained by the connection of the integrated portion of shaft 14 that extends to nut 25. According to some exemplary implementations, both threading 17 and drive connection 16 are of a single integrated structure (i.e., shaft 14). A force applied by spring 22 to nut 25 is directly transferred along shaft 14 from threading 17 to drive connection 16. This force securely maintains drive connection 16 within drive socket 9. This engagement enables transfers of greater amounts of torque from lower shank 700 (i.e., via drive socket 9) to shaft 14 (i.e., via drive connection 16).

According to aspects of some exemplary implementations, drive connection 16 and drive socket 9 have complementary geometries. One or more of a variety of configurations may be provided for engaging drive connection 16 within drive socket 9. For example drives and associated connections may include triangular, square, hexagonal, rectangular, etc. According to aspects of one or more exemplary implementations, a substantially square drive connection 16 and drive socket 9 provide high torque transfer capabilities. Out of a variety of drive types, experimental results demonstrated that square drives and connections were among the most successful at transferring high torque without failure. Drive connection 16 and drive socket 9 may have rounded corners and edges to reduce or distribute stress risers.

According to aspects of one or more exemplary implementations, driver 100 capable of transferring higher torque may be provided with spring 22 having a greater spring constant (i.e., force constant) or otherwise be calibrated with spring 22 exerting greater forces in an initial (rest) state. A more robust spring 22 may Washer 20 and washer 21 may both be provided where spring 22 may have a tendency to grip relative to washer 21. A more robust spring 22 increases the probability of a friction grip relative to washer 21. Provision of additional washer 20 preserves at least one free-spinning structure between spring 22 and upper shank 800.

According to aspects of one or more exemplary implementations, nut 25 may provide a lower portion having outer diameter substantially equal to an inner diameter of spring 22. The lower portion of nut 25 may extend axially through at least a portion of spring 22. The lower portion of nut 25 may maintain relative axial alignment between nut 25 and spring 22 by limiting travel of spring 22 other than by compression thereof.

Figure 6:
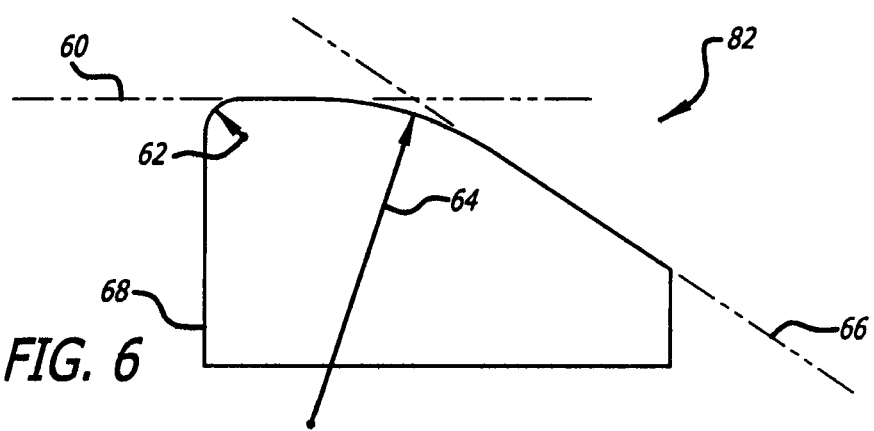
FIG. 6 shows a profile view of some aspects of a tooth from a clutch assembly.
Figure 7:
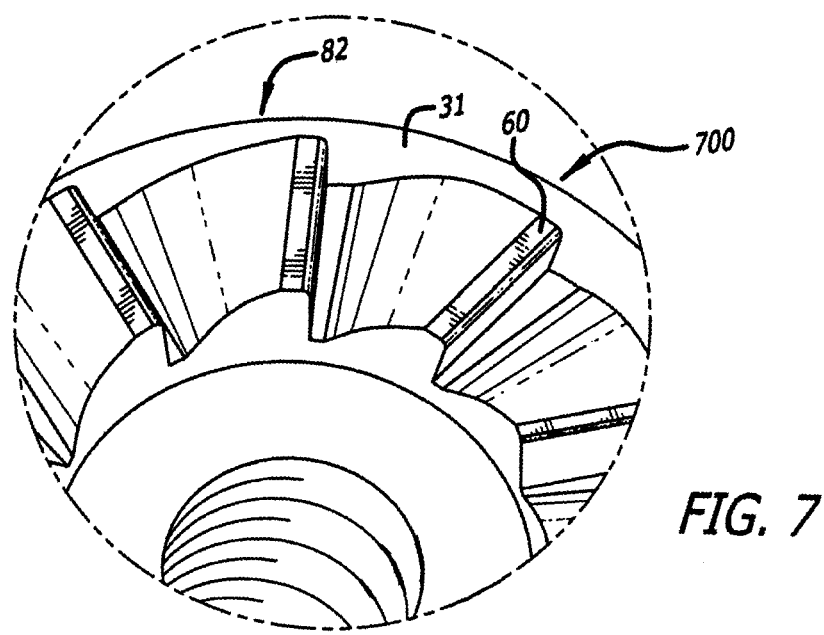
FIG. 7 shows a perspective view of some aspects of the teeth from a clutch assembly.
Figure 8:
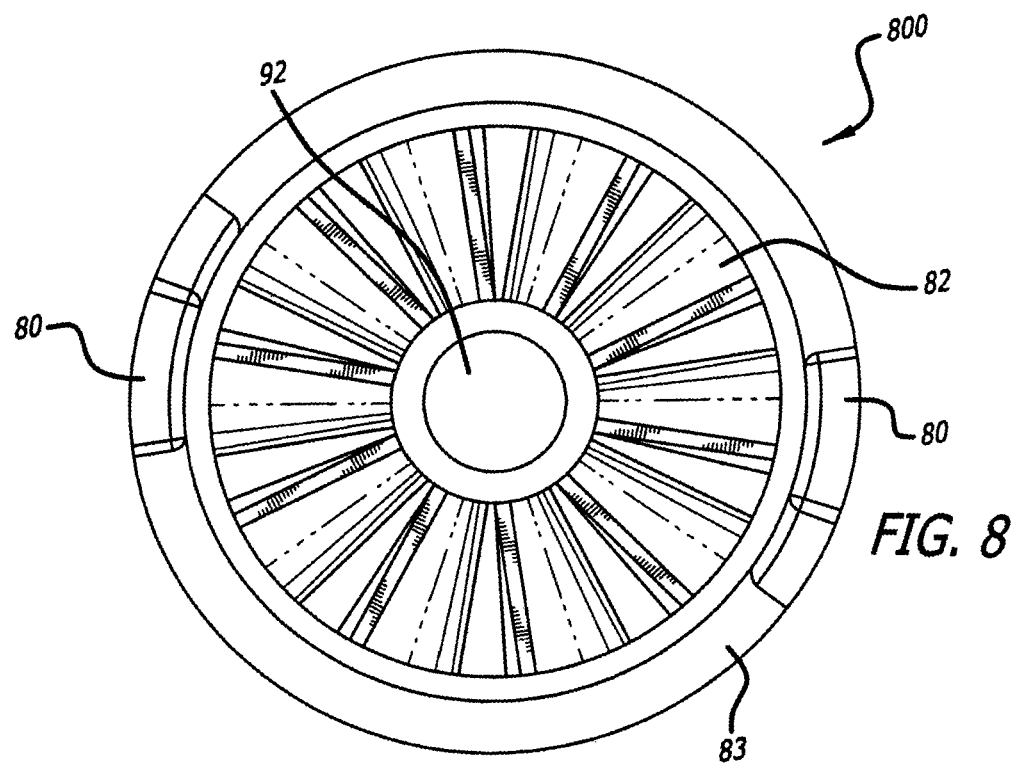
FIG. 8 shows a top view of some aspects of the teeth from a clutch assembly.

According to aspects of one or more exemplary implementations, the plurality of teeth 82 are formed on the top face of lower shank 700 and the bottom face of upper shank 800 to forcibly engage to impart torque from the handle to the workpiece when a torque is applied. Referring to FIGS. 6 and 7, tooth 82 has inclined face 66 that smoothly transitions to substantially flat peak 60, via first radius of curvature 64. Substantially flat peak 60 subsequently transitions smoothly, via second radius of curvature 62, to vertical face 68 that is substantially parallel to the axis of lower shank 700 and upper shank 800. First radius of curvature 64 is typically much larger than second radius of curvature 62.

Experimental results have shown that a tooth having an inclined face that smoothly transitions to a substantially flat face is capable of imparting a substantial increase in torque to a fastener. In one experiment, a ten-fold increase in torque was observed. This increase in torque is due to the frictional forces associated with the smoothly transitioning curve of inclined face 66 of teeth 82.

In a simplified example, when two uniform inclines are frictionally engaged, only one static force, having a single coefficient of static force, is acting against the relative movement of the two inclines. However, when the two inclines are not uniform, more than one coefficient of static force can be observed, thus resulting in a higher disinclination to movement.

According to aspects of one or more exemplary implementations, teeth 82 are circumferentially spaced in a crown gear formation of the top face and bottom face of lower shank 700 and upper shank 800, respectively. Teeth 82 are preferably configured in a spiral formation, as shown in FIG. 7. Each face of lower shank 700 and upper shank 800 has an inner radius and an outer radius and teeth 82 spiral around the inner radius resulting in a larger tooth detail when viewing the tooth from the outer radius relative to the tooth detail when viewing the tooth from the inner radius. The spiral configuration of teeth 82 can also be defined as having a longer inclined face 66 at the edge of the tooth on or near the outer radius relative to inclined face 66 at the edge of the tooth on or near the inner radius of lower shank 700 and upper shank 800. Results have shown that teeth arranged in said spiral configuration provide an increased reliability and/or precision in torque consistency when compared to non-spiral counterparts.

Substantially flat peaks 60 of teeth 82 may be as wide at the inner radius as they are at the outer radius. Alternatively, substantially flat peaks 60 may be wider at the outer radius and taper toward the inner radius.

Vertical faces 68 of teeth 82 of lower shank 700 and upper shank 800 respectively engage when a torque is applied to prevent relative rotation of lower shank 700 and upper shank 800 in one direction. Inclined faces 66 engage to accommodate relative rotation of lower shank 700 and upper shank 800 in an opposite direction.

According to aspects of one or more exemplary implementations, the extent to which threading 17 of shaft 14 is threaded into nut 25 controls the amount of compression or preload on spring 22 which, subsequently, controls the limiting torque required to effect relative rotation of lower shank 700 and upper shank 800. If shaft 14 is more deeply threaded into nut 25, then a higher torque will be required to disengage teeth 82 of lower shank 700 and upper shank 800. If shaft 14 is less deeply threaded into nut 25, then a lower torque will be required to disengage teeth 82 of lower shank 700 and upper shank 800. Accordingly, a predetermined torque limit is selectively programmable. The predetermined torque limit may correspond to a predefined threshold of a workpiece (e.g., a fastener) having a desired level of torque-based installation not to be exceeded.

According to one or more exemplary implementations, when driver 100 is rotated in one direction under an applied torque, shaft 14 will rotate with cylindrical body 6 and handle until a predetermined torque limit is reached. When the predetermined torque limit is reached or exceeded by the applied torque, a biasing force exerted by spring 22 will be overcome, allowing inclined face 66 of upper shank 800 to slide up a respective inclined face 66 of lower shank 700, subsequently snapping each tooth 82 of lower shank 700 into engagement behind a next tooth 82 of upper shank 800. This snapping sound is typically an audible indication to a user that a predetermined torque limit has been reached or exceeded.

When a force beyond the predetermined torque limit is achieved, teeth 82 of lower shank 700 and upper shank 800 will continue to disengage, resulting in rotation of the handle with no further rotation of workpiece-engaging tip 12. Thus, the handle will continue to rotate, disengaging teeth 82 with every rotational movement that will not impart continued force beyond a predefined threshold to the fastener.

According to one or more exemplary implementations, when driver 100 is rotated in the opposite direction, the handle rotates in reverse a predetermined distance from a locked position without subsequent reverse rotation of workpiece-engaging tip 12. However, when protrusion 85 travels the provided distance within recess 80 and locks against the opposite end of recess 80, driver 100 will operate as a standard driver with no torque-limiting feature since engaging vertical face 68 will force relative rotation of lower shank 700 and upper shank 800 in the opposite direction without any torque-limiting feature.

According to aspects of one or more exemplary implementations, the disposable torque-limiting driver of the present disclosure is capable of imparting torques of up to about 120 inch-pounds. For example, the torque output range may be selected between about 70 inch-pounds and about 120 inch-pounds. Typically, the torque requirement is different for different operations and for different implants. For example, applications may include those in the field of orthopedic surgery, construction and emplacement of implants, etc. Therefore, in some instances, the predetermined torque limit may be at least about 1 inch-pound. In other instances, the predetermined torque limit may be between about 5 inch-pounds and about 150 inch-pounds, depending on an implant's specifications. In other instances, the predetermined torque limit may be between about 70 inch-pounds and about 120 inch-pounds, depending on an implant's specifications.

According to one or more exemplary implementations, as shown in FIG. 3, shaft 14 may be cannulated to include lumen 15. Lumen 15 may extend along the entire length of shaft 14, with a top opening "B" and a bottom opening "C" (at workpiece-engaging tip 12), said openings in some instances being in fluid communicating with each other. Body 6 may provide access to lumen 15, such as via aperature "A" of cap 2. According to some exemplary implementations, lumen 15 may accommodate one or more devices or materials for use in tandem with the torque capabilities of driver 100. According to some exemplary implementations, a guidewire to aide in driver alignment may be provided through lumen 15. According to some exemplary implementations, lumen 15 may accommodate a tube delivering a biologic material to be dispensed before, during, or after torque is applied. For example, the biologic material could be an adhesive to assist in locking or staking a fastener to which torque was applied. By further example, the biologic material may assist in stimulation of bone growth (i.e., growth stimulant). Lumen 15 may accommodate one or more devices. Such devices may include a sound-emitting device (e.g., ultrasound, etc.), a radiation-emitting device (e.g., light, laser, LED, etc.), a drilling device, a cutting device, an ablation device, a curing device, a retrieval device, an aspiration device, a suction device, an irrigation device, a gasification device, a cooling device, a heating device, an optical device (e.g., scope for viewing, etc.), inter alia.

Figure 9:
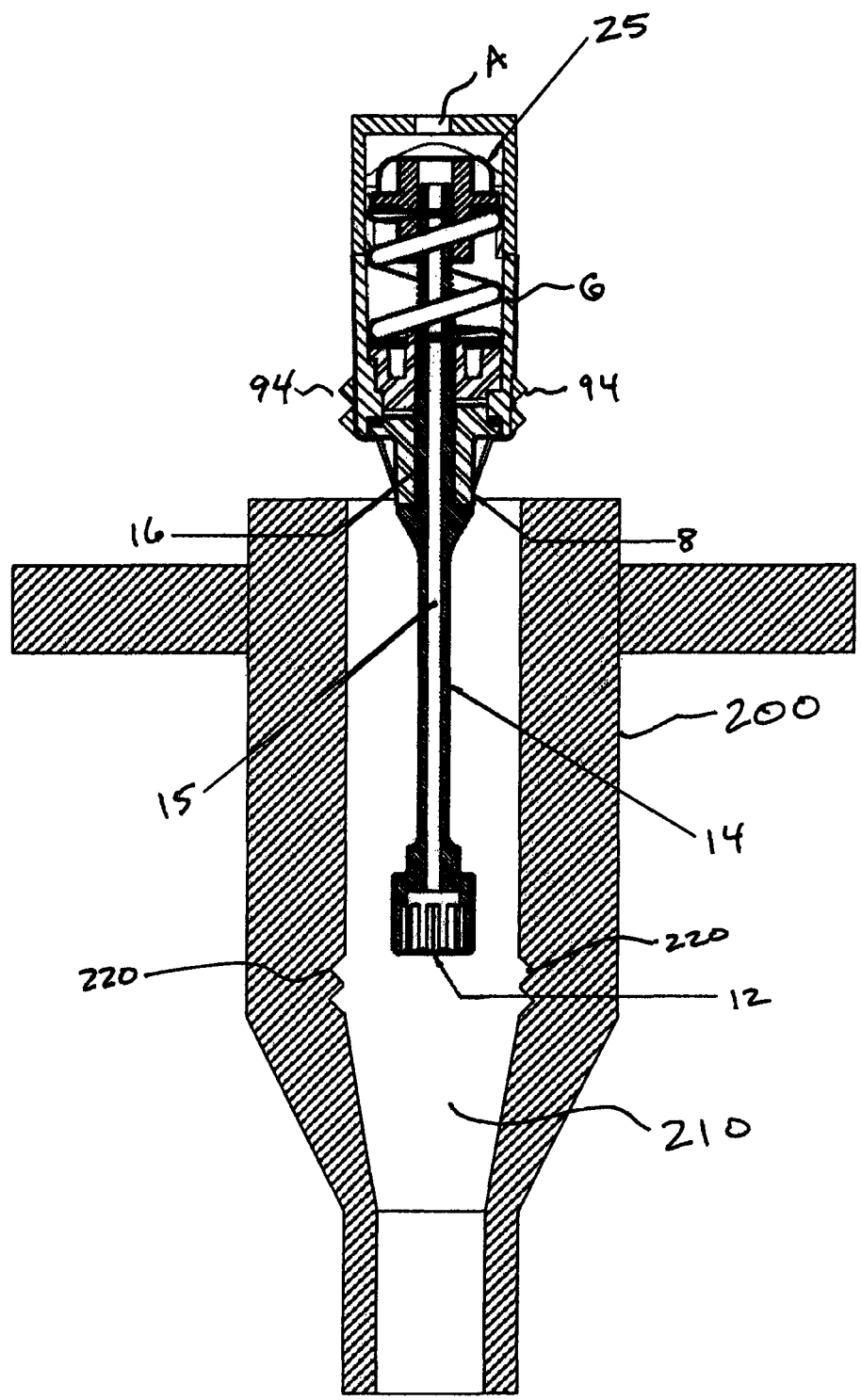
FIG. 9 shows a cross sectional view of some aspects of a driver and an operation tool.

According to one or more exemplary implementations, as shown in FIG. 9, driver 100 may be configured to interface with at least one other device. For example, as shown in FIG. 9, driver 100 may be a device that selectably fits within channel 210 of operation tool 200. Operation tool 200 may be configured to accept one or more devices, including driver 100, wherein such devices are selectably interchangeable during a procedure. According to aspects of one or more exemplary implementations, operation tool 200 may include female interface 220 configured to mate with male interface 94 of driver 100. Male interface 94 and female interface 220 may provide selectably secure engagement between driver 100 and operation tool 200 via threading, interference fitting, locks, gears, snaps, pins, and the like. Male interface 94 and female interface 220 may limit one or more of relative axial motion, relative radial motion, and relative rotational motion between driver 100 and operation tool 200.

According to aspects of one or more exemplary implementations, driver 100 may deliver torque while within operation tool 200. According to aspects of one or more exemplary implementations, driver 100 is rotatable according to the rotation of operation tool 200. For example, body 6 of driver 100 may be rotationally fixed relative to operation tool 200, such that rotation of operation tool 200 results in rotation of body 6, imparting programmable torque at tip 12. According to aspects of one or more exemplary implementations, driver 100 is rotatable independent of the rotation of operation tool 200. For example, body 6 of driver 100 may be rotated within operation tool 200 while operation tool 200 is held in place, wherein driver 100 imparts programmable torque at tip 12.

According to one or more exemplary implementations, driver 100 may be interchanged within operation tool 200 with other devices. Operation tool 200 may provide a stable platform for a variety of devices to perform designated functions. Across the variety of devices, operation tool 200 may maintain constant or selectable location and orientation for controllably aligning and delivering the devices to a desired location.

In some instances, a torque-limiting driver, such as driver 100, may be prepackaged with an implant provided for one-time use. Such a methodology matches the driver that will impart a required amount of torque with the implant.

In other instances, the driver 100 may be reusable. Shaft 14 may be interchangeably fixed relative to nose cone 8 for the accommodation of multiple workpiece-engaging tips 12. It is also to be appreciated that the handle of the driver is not limited to a T-shape and may be provided in any other suitable configuration.

While the method and agent have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these disclosure(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular implementation, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative implementations.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. A torque-limiting driver comprising:
    a body having a handle and a hollow cylindrical portion, the body further comprising a circumferential flange extending radially inward within the hollow cylindrical portion;
    an upper cylindrical shank comprising a plastic material or a composite including plastic;
    a lower cylindrical shank comprising a plastic material or a composite including plastic and having a square drive socket;
    a nut;
    a spring between the upper cylindrical shank and the nut, wherein the spring is configured to apply a force across the upper cylindrical shank and the lower cylindrical shank;
    a shaft having a workpiece-engaging tip and a square drive connection engaged within the square drive socket of the lower cylindrical shank, the shaft extending axially through the lower cylindrical shank, the upper cylindrical shank, and the spring and connected to the nut, the square drive connection placed at a medial segment of the shaft, and the shaft having a lumen extending across an axial length of the shaft;
    wherein the upper cylindrical shank and the lower cylindrical shank engage for relative rotation, and wherein the upper cylindrical shank and the lower cylindrical shank disengage when a predetermined torque limit is exceeded; and
    wherein the lower cylindrical shank and the upper cylindrical shank each comprise a circumferential rim extending radially outward at the ends where the lower cylindrical shank and the upper cylindrical shank engage with each other, with the circumferential flange of the body disposed between the circumferential rims.

2. The torque-limiting driver of claim 1, wherein the lumen encloses a guidewire advanceable within the lumen.

3. The torque-limiting driver of claim 1, wherein the shaft includes a threading that is threaded onto the nut.

4. The torque-limiting driver of claim 1, wherein a force provided by the spring securely maintains the square drive connection of the shaft engaged within the square drive socket of the lower cylindrical shank.

5. The torque-limiting driver of claim 1, wherein the nut includes a lower portion having an outer diameter substantially equal to an inner diameter of the spring and extending axially through at least a portion of the spring.

6. The torque-limiting driver of claim 1, further comprising at least two washers between the spring and the upper cylindrical shank.

7. The torque-limiting driver of claim 1, further comprising a washer between the lower cylindrical shank and the body.

8. The torque-limiting driver of claim 1, further comprising a washer between the spring and the nut.

9. The torque-limiting driver of claim 1, wherein the predetermined torque limit is at least 1 inch-pound.

10. The torque-limiting driver of claim 1, wherein the predetermined torque limit is between about 70 inch-pounds and about 150 inch-pounds.

11. The torque-limiting driver of claim 1, wherein the lumen encloses a tube advanceable within the lumen.

12. The torque-limiting driver of claim 11, wherein the tube is configured to deliver a biologic material.

13. The torque-limiting driver of claim 12, wherein the biologic material is an adhesive.

14. The torque-limiting driver of claim 12, wherein the biologic material is a growth stimulant.

15. The torque-limiting driver of claim 1, wherein the upper cylindrical shank and the lower cylindrical shank each have a plurality of teeth and an axial bore, the teeth having a vertical face, an inclined face and a substantially flat peak, wherein the inclined face is defined by a first radius of curvature that transitions to the substantially flat peak and wherein the teeth spiral around the axial bore.

16. The torque-limiting driver of claim 15, wherein the substantially flat surface is wider at the outer radius than at the inner radius and wherein the substantially flat surface is perpendicular to the axis of the upper and lower shank.

17. The torque-limiting driver of claim 15, wherein the vertical face terminates in a second radius of curvature that transitions to the substantially flat peak and wherein the second radius of curvature is smaller than the first radius of curvature.

18. The torque-limiting driver of claim 17, wherein the transitions from the first radius of curvature and second radius of curvature to the substantially flat peak are smooth.

19. A method, comprising:
    providing to a workpiece a torque-limiting driver comprising: a body having a handle and a hollow cylindrical portion, the body further comprising a circumferential flange extending radially inward within the hollow cylindrical portion; an upper cylindrical shank comprising a plastic material or a composite including plastic; a lower cylindrical shank comprising a plastic material or a composite including plastic and having a square drive socket; a nut; a spring between the upper cylindrical shank and the nut, wherein the spring is configured to apply a force across the upper cylindrical shank and the lower cylindrical shank; a shaft having a workpiece-engaging tip and a square drive connection engaged within the square drive socket of the lower cylindrical shank, the shaft extending axially through the lower cylindrical shank, the upper cylindrical shank, and the spring and connected to the nut, the square drive connection placed at a medial segment of the shaft, and the shaft having a lumen extending across an axial length of the shaft; wherein the lower cylindrical shank and the upper cylindrical shank each comprise a circumferential rim extending radially outward at the ends where the lower cylindrical shank and the upper cylindrical shank engage with each other, with the circumferential flange of the body disposed between the circumferential rims;
    applying an applied torque to the torque-limiting driver, whereby the upper cylindrical shank and the lower cylindrical shank engage for relative rotation if the applied torque does not exceed the predetermined torque limit, and whereby the upper cylindrical shank and the lower cylindrical shank disengage if the applied torque exceeds the predetermined torque limit; and delivering a device or material to the workpiece through the lumen.

20. The method of claim 19, wherein the material is an adhesive.

21. The method of claim 19, wherein the material is a growth stimulant.

22. The method of claim 19, wherein the device is one of sound emitting, light emitting, radiation emitting, drilling, cutting ablating, curing, grabbing, aspirating, suctioning, irrigating, gasification, cooling, heating and optical for viewing.

23. A method, comprising:

providing to a workpiece a torque-limiting driver comprising: a body having a handle and a hollow cylindrical portion, the body further comprising a circumferential flange extending radially inward within the hollow cylindrical portion; an upper cylindrical shank comprising a plastic material or a composite including plastic; a lower cylindrical shank comprising a plastic material or a composite including plastic and having a square drive socket; a nut; a spring between the upper cylindrical shank and the nut, wherein the spring is configured to apply a force across the upper cylindrical shank and the lower cylindrical shank; a shaft having a workpiece-engaging tip and a square drive connection engaged within the square drive socket of the lower cylindrical shank, the shaft extending axially through the lower cylindrical shank, the upper cylindrical shank, and the spring and connected to the nut, the square drive connection placed at a medial segment of the shaft, and the shaft having a lumen extending across an axial length of the shaft; wherein the lower cylindrical shank and the upper cylindrical shank each comprise a circumferential rim extending radially outward at the ends where the lower cylindrical shank and the upper cylindrical shank engage with each other, with the circumferential flange of the body disposed between the circumferential rims; wherein the upper cylindrical shank and the lower cylindrical shank engage for relative rotation, and wherein the upper cylindrical shank and the lower cylindrical shank disengage when a predetermined value of torque is exceeded;

aligning the torque-limiting driver relative to the workpiece by use of a guidewire delivered through the lumen of the shaft; and, applying an applied torque to the torque-limiting driver, whereby the upper cylindrical shank and the lower cylindrical shank engage for relative rotation if the applied torque does not exceed the predetermined torque limit, and whereby the upper cylindrical shank and the lower cylindrical shank disengage if the applied torque exceeds the predetermined torque limit.

\* \* \* \* \*